(12) United States Patent
Munson

(10) Patent No.: US 10,092,615 B2
(45) Date of Patent: Oct. 9, 2018

(54) NUTRITIONAL SUPPLEMENTS FOR IMPROVING MALE FERTILITY

(71) Applicant: Fairhaven Health, LLC, Bellingham, WA (US)

(72) Inventor: Suzanne Munson, Bellingham, WA (US)

(73) Assignee: Fairhaven Health, LLC, Bellingham, WA (US)

( * ) Notice: Subject to any disclaimer, the term of this patent is extended or adjusted under 35 U.S.C. 154(b) by 95 days.

(21) Appl. No.: 15/143,545

(22) Filed: Apr. 30, 2016

(65) Prior Publication Data

US 2017/0312328 A1    Nov. 2, 2017

(51) Int. Cl.

| | |
|---|---|
| *A61K 38/43* | (2006.01) |
| *A61K 31/205* | (2006.01) |
| *A61K 31/122* | (2006.01) |
| *A61K 31/714* | (2006.01) |
| *A61K 31/195* | (2006.01) |
| *A61K 36/87* | (2006.01) |
| *A61K 31/198* | (2006.01) |
| *A61K 31/01* | (2006.01) |
| *A61K 31/375* | (2006.01) |
| *A61K 31/593* | (2006.01) |
| *A61K 31/355* | (2006.01) |
| *A61K 31/51* | (2006.01) |
| *A61K 31/525* | (2006.01) |
| *A61K 31/455* | (2006.01) |
| *A61K 31/4188* | (2006.01) |
| *A61K 33/18* | (2006.01) |
| *A61K 33/30* | (2006.01) |
| *A61K 33/00* | (2006.01) |
| *A61K 33/34* | (2006.01) |
| *A61K 33/32* | (2006.01) |
| *A61K 33/24* | (2006.01) |
| *A23L 1/305* | (2006.01) |
| *A23L 1/302* | (2006.01) |
| *A23L 1/30* | (2006.01) |
| *A23L 1/304* | (2006.01) |
| *A23L 1/29* | (2006.01) |
| *A61K 45/06* | (2006.01) |
| *A61K 31/07* | (2006.01) |
| *A61K 31/197* | (2006.01) |
| *A61K 31/4415* | (2006.01) |
| *A61K 33/04* | (2006.01) |
| *A23L 33/10* | (2016.01) |
| *A23L 33/15* | (2016.01) |
| *A23L 33/16* | (2016.01) |
| *A23L 33/175* | (2016.01) |

(52) U.S. Cl.
CPC .............. *A61K 36/87* (2013.01); *A23L 1/296* (2013.01); *A23L 1/30* (2013.01); *A23L 1/302* (2013.01); *A23L 1/3002* (2013.01); *A23L 1/304* (2013.01); *A23L 1/3051* (2013.01); *A23L 33/10* (2016.08); *A23L 33/15* (2016.08); *A23L 33/16* (2016.08); *A23L 33/175* (2016.08); *A61K 31/01* (2013.01); *A61K 31/07* (2013.01); *A61K 31/122* (2013.01); *A61K 31/197* (2013.01); *A61K 31/198* (2013.01); *A61K 31/205* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/593* (2013.01); *A61K 31/714* (2013.01); *A61K 33/00* (2013.01); *A61K 33/04* (2013.01); *A61K 33/18* (2013.01); *A61K 33/24* (2013.01); *A61K 33/30* (2013.01); *A61K 33/32* (2013.01); *A61K 33/34* (2013.01); *A61K 45/06* (2013.01); *A23V 2002/00* (2013.01)

(58) Field of Classification Search
CPC .. A61K 31/205; A61K 31/122; A61K 31/714; A61K 31/195; A61K 36/87
See application file for complete search history.

(56) References Cited

U.S. PATENT DOCUMENTS

2008/0020018 A1*  1/2008  Moodley .............. A61K 9/5073
                                                           424/433

OTHER PUBLICATIONS

Male Fertility Supplement Starter Pack. Datasheet [online]. Fairhaven Health, Jul. 7, 2015 [retrieved on Dec. 21, 2017]. Retrieved from the Internet: <URL: https://web.archive.org/web/20140707093710/http://www.fairhavenhealth.com/male-fertility.html>.*

Agarwal, A. and Sekhon, L., The role of antioxidant therapy in the treatment of male infertility. Human Fertility, vol. 13, No. 4 (2010) pp. 217-225.*

Ghareeb, D., and Sarhan, E., Role of oxidative stress in male fertility and idiopathic infertility: Causes and treatment. Journal of Diagnostic Techniques & Biomedical Analysis, vol. 3, No. 1 (2014) pp. 1-12.*

Agarwal et al., Utility of antioxidants during assisted reproductive techniques: an evidence based review. Reproductive Biology and Endocrinology, vol. 12, No. 112 (2014) pp. 1-19.*

(Continued)

*Primary Examiner* — Kara D Johnson
(74) *Attorney, Agent, or Firm* — Don D. Cha; Hamilton DeSanctis & Cha, LLP.

(57) ABSTRACT

The present invention relates to a fertility-enhancing composition for human male fertility therapy and a method for using the same to improve or enhance human male fertility. The nutritional supplement composition of the invention includes an effective amount of L-carnitine, coenzyme Q10, vitamin $B_{12}$, N-acetyl L-cysteine, and grape seed extract.

15 Claims, No Drawings

(56) References Cited

OTHER PUBLICATIONS

Safarinejad, M. and Safarinejad, S., Efficacy of selenium and/or n-acetyl-cysteine for improving semen parameters in infertile men: A double-blind, placebo controlled, randomized study. The Journal of Urology, vol. 181, No. 2 (Feb. 2009) pp. 741-751.*
Meletis, D. and Barker, J., Natural ways to enhance male fertility. Alternative & Complementary Therapies (Feb. 2004) pp. 22-27.*
Zhai et al., Effects ofmolybdenum on sperm quality and testis oxidative stress. Systems Biology in Reproductive Medicine, vol. 59, No. 5 (online May 8, 2013) pp. 251-255. (Year: 2013).*
Bachmanov et al., Food intake, water intake, and drinking spout side preference of 28 mouse strains. Behavioral Genetics, vol. 32, No. 6 (2002) pp. 435-443. (Year: 2002).*

\* cited by examiner

NUTRITIONAL SUPPLEMENTS FOR IMPROVING MALE FERTILITY

FIELD OF THE INVENTION

The present invention relates to a fertility-enhancing composition for human male fertility therapy and a method for using the same to improve human male fertility.

BACKGROUND OF THE INVENTION

It is estimated approximately 30% of cases of couple infertility are due to a male factor. Several conditions can interfere with spermatogenesis and reduce sperm quality and production. Oxidative stress is a leading cause of male infertility, as it leads to decreased sperm count and motility and causes damage to sperm DNA.

An estimated six percent of adult males are thought to be infertile. Infertility is defined generally as the inability to achieve a pregnancy after one year of unprotected intercourse. Conception is normally achieved within 12 months in 80-85 percent of couples using no contraceptive measures; thus, an estimated 15 percent of couples attempting their first pregnancy will have difficulty conceiving. While certain cases of male infertility are due to anatomical abnormalities such as varicoceles, ductal obstructions, or ejaculatory disorders, it has been shown that an estimated 40-90 percent of cases are due to deficient sperm production of unidentifiable origin.

A normal semen sample have a volume of 1.5-5.0 ml, with greater than 20 million sperm/mL. Without being bound by any theory, it is believed that to achieve conception the number of abnormally shaped sperm should be less than 40 percent, with 50 percent or more of the sperm sample demonstrating proper motility.

Unfortunately, there is a growing body of scientific evidence supporting the idea that sperm counts in male have declined considerably over the last 50 years. Three recent reports also found semen quality has declined among donors over the last 20 years. Because the decline in sperm production is relatively recent, it is believed that a combination of environmental, lifestyle, and dietary factors may be interfering with spermatogenesis.

Oxidative stress has been shown to be a major cause of male infertility. A large proportion of infertile men have elevated levels of seminal reactive oxygen species (ROS). High concentrations of ROS cause sperm pathology such as ATP depletion leading to insufficient axonemal phosphorylation, lipid peroxidation and loss of motility and viability.

A commonly assigned U.S. Pat. No. 8,974,838, issued Mar. 10, 2015, which is incorporated herein by reference in its entirety, provides a nutritional supplement comprising a sperm count enhancing dose of *Lepidium meyenii* to improve male infertility. However, there still is a need for other nutritional supplements for enhancing male fertility, especially in which the male infertility is believed to be due to oxidative stress and/or reduced sperm motility.

SUMMARY OF THE INVENTION

The present invention provides a nutritional supplement composition for improving male fertility. Without being bound by any theory, it is believed that the composition of the invention is believed to be particularly useful in improving male fertility where the cause of male infertility is due primarily due to oxidative stress.

The nutritional supplement composition of the invention comprises an effective amount of N-acetyl L-cysteine for improving male fertility. The composition of the invention can also include at least one antioxidant, vitamins, minerals or a combination thereof. In some embodiments, the composition of the invention also includes one or more of the following ingredients: L-carnitine, coenzyme Q10, vitamin $B_{12}$, and grape seed extract.

The present invention also provides a method for improving fertility in a male human. The method of the invention comprises administering to a male human an effective amount of a composition of the invention. Typically, the composition of the invention is administered to the male human for at least 3 months.

DETAILED DESCRIPTION OF THE INVENTION

Some aspects of the invention provide an alternative therapy for male infertility. The effects of the components of the composition of the invention have been shown by various researchers, but never before has a composition been provided that enhances or increases male infertility that is believed to be due to oxidative stress and reduced sperm motility.

In the following description, numerous specific details are set forth in order to provide a more thorough description of the present invention. It will be apparent, however, to one skilled in the art, that the present invention may be practiced without these specific details. Moreover, it is to be understood that the present disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally. In this manner, a wide variety of combination of embodiments and aspects of the invention are possible.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article "a" (meaning "one") is used herein to denote the start of a range beginning with that number (which may be a range having an upper limit or no upper limit, depending on the variable being defined). For example "at least one" or "at least a" means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm. The term "about" when referring to a number refers to ±20%, typically ±10%, and often ±5% of the numeric value. The term "or" is used herein as a conjunction used to link alternatives in a series of alternatives. The term "and/or" is used herein as a conjunction meaning that either or both of two options may be valid. The term "conception" refers to the beginning of pregnancy as marked by the formation of a zygote. "Possibility of conception" refers to the likelihood of conception occurring during normal sexual activity.

"Normospermia" refers to the production of spermatozoa normal in number and motility. "Oligospermia" refers to the production of fewer sperm than normal. "Asthenospermia" refers to the loss or reduction of spermatozoan motility. "Azoospermia" refers to the production of no sperm at all. "Teratospermia" refers to the production of malformed spermatozoa in the semen. "Oligoasthenospermia" refers to the production of fewer sperm than normal with decreased motility. "Sperm count" refers to the number of sperm counted in a standard volume of semen. "Sperm quality" refers to the percentage of viable sperm and the morphology (shape) of the sperm. "Sperm motility" refers to the measurement of the sperms ability to "swim" through a volume, usually in a forward direction.

One aspect of the invention provides a composition for improving human male fertility. The composition may be is in a dosage form of a tablet, capsule, liquid, liposome, inhalant, sublingual tablet, suppository, oral spray and dermal patch and may further comprise a pharmaceutically acceptable carrier. As used herein, the term "improving human male fertility" refers to a statistically significant increase in human male fertility by at least about 5%, typically by at least about 10%, often by at least about 25%, more often by at least about 30%, and most often by at least about 50% resulting from administration of a composition of the invention. The improvement in male human fertility can be measured, for example, by a typical experimental procedure known to one skilled in the art in determining efficacy of a drug or a nutritional supplement. One frequently used method involves administering a composition of the invention to a group of male human individuals (i.e., "test group") and administering a placebo composition to another group of male human individuals (i.e., "control group"). By comparing the fertility efficacy between the test group and the control group, one can determine the efficacy of a composition of the invention in improving male fertility.

In some embodiments, the control group and the test group are selected by matching one or more characteristics, such as age, race, or any relevant biological or sociological factor that may affect the control group and the test group (e.g., preexisting conditions, consumption of particular substances such as alcohol, levels of other biological or physiological factors). The number of matched individuals from whom control group must be obtained to establish a suitable control level (e.g., a population) can be determined by those of skill in the art, but should be statistically appropriate to establish a suitable "baseline" or control data for comparison with the test group to be evaluated. The values obtained from the control group and the test group are statistically processed using any suitable method of statistical analysis to establish a suitable comparative data using methods standard in the art.

The sperm motility increase due to using a composition of the invention can be determined, for example, by comparing the sperm motility of the male subject prior to being on the regiment of taking the composition of the invention and after being on the nutritional supplement regiment for a given period of time, e.g., one month, two months, three months, four months, five months, six months, etc.

Methods of improving male fertility include administering the composition of the invention to a male subject for a period of time sufficient to improve human male fertility. In some embodiments, compositions of the invention include comprehensive vitamins and minerals to provide antioxidant protection and/or sperm motility. Composition of the invention has shown to promote male fertility and overall reproductive health by decreasing oxidative stress, improving nutritional status, and/or improving sperm function. Typically, the male subject begins taking the composition of the invention at least one month, typically at least two month, and often three to six months before trying to conceive naturally or initiating artificial reproductive therapy (e.g., in vitro fertilization).

Some of the benefits of the composition of the invention include, but are not limited to, formulated to meet standards recommended by fertility experts, designed to be used in conjunction with assisted reproductive technologies, provides effective dosages of key fertility-enhancing ingredients, including coenzyme Q10, L-carnitine, arginine, zinc, selenium, vitamin E, lycopene, etc. In some embodiments, composition of the invention includes other vitamins and minerals. It should be noted that the composition of the invention excludes *Lepidium meyenii*. Thus, unlike the commonly assigned U.S. Pat. No. 8,974,838, no *Lepidium meyenii* is present in the composition of this invention.

Antioxidants play an important role in protecting semen from reactive oxygen species ("ROS"). In fact, administration of antioxidants to male human has been shown to improve and/or enhance male fertility, for example, in case of idiopathic oligoasthenoteratozoospermia. Imamovic Kumalic S. et al., *Biomed Res Int.*, 2014, p. 426951. Thus, the composition of the invention comprises one or more of the following antioxidants: vitamin A (e.g., as beta-carotene), vitamin C, vitamin E, QUATREFOLIC® (glucosamine salt of (6S)-5-methyltetrahydrofolate), selenium, coenzyme Q10, lycopene and grape seed extract. In one particular embodiment, the composition of the invention includes all of the following antioxidants: vitamin A, vitamin C, vitamin E, QUATREFOLIC®, selenium, coenzyme Q10, lycopene and grape seed extract.

Other components that may optionally be present include, but are not limited to, other vitamins (such as vitamin D3, vitamin K, B complex vitamins, etc.), minerals (such as iodine, chromium, manganese, molybdenum, copper and zinc), and others such as N-acetyl L-cysteine, benfotiamine, L-arginine, etc.

In some aspects of the invention, composition of the invention includes N-acetyl L-cysteine. It has been shown that the presence of N-acetyl L-cysteine, when used in conjunction with antioxidants, improves live birth rate of men/couples. Particularly those undergoing artificial reproductive therapy.

In another embodiment, the composition of the invention includes L-carnitine, e.g., in the form of L-carnitine tartrate. It has been shown that L-carnitine is an essential cofactor for mitochondrial, β-oxidation of long-chain fatty acids, and is known to play important roles in sperm maturation and metabolism when spermatozoa pass and acquire motility in the epididymis. Azoospermia occurred in the epididymis in the juvenile visceral steatosis (JVS) mice, which are OCTN2 dysfunction mice caused by mutations in the gene encoding OCTN2, have been used for animal models of primary systemic carnitine deficiency. Animals used in this study were wild-type (C57BL/6 J) mice (n=4) and JVS mice (n=4). As measured by polyclonal antibodies, OCTN2 was localized on the apical membrane of the principal cells of distal corpus and cauda epididymides. These results suggest that OCTN2 functions as a carnitine transporter between the epithelium and the lumen in distal corpus and cauda epididymides and provides a clue as to why obstructive azoospermia is induced in distal parts of epididymis. Yakushiji K, et al., *Int J Urol.*, 2006, 13(4), 420-6.

The benefits of L-carnitine in improving sperm quality is well-studied. See, for example, Ng, C M, et al., *Ann NY Acad. Sci.*, 2004, 1033, 177-88. It is believed L-carnitine may also improve sperm motility. Garolla, A. et al, *Fertil Steril.*, 2005, 83(2), 355-61. Spermatozoan maturation, motility, and fertility are, in part, dependent upon the progressive increase in epididymal and spermatozoal carnitine, critical for mitochondrial fatty acid oxidation, as sperm pass from the caput to the cauda of the epididymis. It has been suggested that defective sperm carnitine transport may be a potentially treatable etiologies of male infertility by administration of L-carnitine supplementation.

Some studies have shown carnitine levels and supplementation to correlate with numerous parameters of sperm function. For example, in one study involving 170 infertile men who received either L-carnitine 1 g/day or acetyl-L-carnitine 500 mg/day for six months, there was a significant correlation between seminal carnitine concentration and sperm concentration, total sperm count, sperm total motility, rapid forward progression, live sperm count, membrane function, nuclear DNA integrity, capacity for cervical mucus penetration, linearity of spermatic movement, and amplitude of lateral sperm head movement ($p<0.0001$) in the entire study population. De Rosa, M. et al., *Drugs R&D*, 2005, 6(1), 1-9.

In another study of 64 infertile men, the Pearson coefficients of correlation of the L-carnitine level with sperm motility, vitality and concentration were 0.161 (P=0.235), 0.114 (P=0.370) and 0.637 (P<0.001), those of free seminal carnitine with sperm motility and vitality were 0.325 (P=0.024) and 0.316 (P=0.029), respectively, with the oligozoospermia group excluded, and that of partial correlation between the concentrations of seminal L-carnitine and sperm was 0.641 (P<0.001). These results suggest the level of seminal plasma L-carnitine is positively correlated with sperm motility and vitality, and more significantly with sperm concentration. Tang, L F. et al., *Zhonghua Nan Ke Xue*, 2008, 14(8), 704-8. Other studies have shown carnitine levels to be more closely associated with sperm quality than other sperm parameters. See, for example, Lenzi, A. et al., *Fertil Steril.*, 2003, 79(2).

In a meta-analysis of nine randomized clinical trials, administration of L-carnitine or acetyl-L-carnitine therapy compared to placebo showed significant improvement in pregnancy rate (OR=4.10, 95% CI (2.08, 8.08), p<0.0001), total sperm motility (WMD=7.43, 95% CI (1.72, 13.14), p=0.04, forward sperm motility (WMD=11.83, 95% CI (0.49, 23.16), p=0.04) and atypical sperm cell (WMD=−5.72, 95% CI (−7.89, −3.56), p<0.00001) without significant difference in the sperm concentration (WMD=5.69, 95% CI (−4.47, 15.84), p=0.27) and semen volume (WMD=0.28, 95% CI (−0.02, 0.58), p=0.07). Thus, it is believed that L-carnitine and/or acetyl-L-carnitine is effective in improving pregnancy rate and sperm kinetic features in patients affected by male infertility. Zhou X. et al., *Suppl. I Asia Pac J Clin Nutr.*, 2007, 16, 383-90. Other studies have shown the level of free L-carnitine in the seminal plasma of the fertile men was significantly higher than that of the infertile men (P<0.01). It was found that the lower the sperm concentration, the weaker the sperm vitality, the more significant the difference. The level of free L-carnitine in the semen was also positively correlated with sperm concentration, and sperm motility and vitality.

Without being bound by any theory, it is believed that one the main functions of carnitine in the epididymis is to provide an energetic substrate for spermatozoa. It may also be involved in the successful maturation of sperm. This is especially important since epididymal sperm use fatty acid oxidation as their main source of energy metabolism, and thus tend to concentrate carnitine while in the epididymis, as carnitine is necessary for transport of fatty acids into the mitochondria. Low levels of carnitine reduce fatty acid concentrations within the mitochondria, leading to decreased energy production and potential alterations in sperm motility.

The composition of the invention also includes coenzyme Q10. Coenzyme Q10 has been shown by several researchers to improve sperm motility. Coenzyme Q10 is concentrated in the mitochondrial mid-piece, where it is involved in energy production. It also functions as an antioxidant, preventing lipid peroxidation of sperm membranes. In one study, when sperm samples from 22 asthenospermic men were incubated in vitro with 50 µM Coenzyme Q10 significant increases in motility were observed. In another study, coenzyme Q10 was given to 17 infertile patients for a mean 103 days, and although there were no significant changes in standard sperm parameters, there was a significant improvement in fertilization rate (p<0.05). Sinclair, S., *Alt Med Review*, 2000, 5(1), 28-38. Another study showed significant correlations between higher Co Q10 with both sperm count and motility.

Some of the other components that can be present in the composition of the invention and there role in improving or enhancing male fertility is provided below. Vitamin A (e.g., as beta-carotene). Vitamin A is a known antioxidant. It also provides sperm nutritional support. The presence of vitamin A also improves in vitro fertilization outcomes when used in conjunction with other antioxidants. The amount of vitamin A present in a single serving size of a composition of the invention is at least about 2,000 IU, typically at least about 3,000 IU, often at least about 4,000 IU and more often at least 5,000 IU. As discussed in more detail below, the term "single serving size" is not synonymous with the term "single dose" or "single unit" or "single dosage form". The term "single serving size" refers to a recommended amount of intake per day. Thus, the term "single serving size" generally refers to the amount of a given component provided to male human in a given day by compositions of the invention. While the "single serving" is administered once daily, it may be administered in portions throughout the day. Thus, the amount of "single serving size" simply refers to the amount of a given component of the composition of the invention that is provided in a given day.

Vitamin C (as ascorbic acid). Vitamin C is also a known antioxidant. It too provides sperm nutritional support. The presence of vitamin C compositions of the invention improves sperm motility and concentration. In addition, vitamin C improves in vitro fertilization outcomes when used in conjunction with other antioxidants. The amount of vitamin C present in a single serving size of a composition of the invention is at least about 50 mg, typically at least about 75 mg, often at least about 100 mg and more often at least 120 mg.

Vitamin D3 (e.g., presented as cholecalciferol) provides sperm nutritional support. It is believed to be essential for the development of sperm cell nucleus. Thus, the presence of vitamin D3 improves semen quality and count and also supports testosterone levels. It should be noted that vitamin D3 deficiency is widespread, particularly in northern U.S. regions. The amount of vitamin D3 present in a single serving size of a composition of the invention is at least about 500 IU, typically at least about 750 IU, often at least about 1,000 IU and more often at least 1,200 IU.

Vitamin E (e.g., 87.5% as d-α-tocopheryl succinate and 12.5% as mixed tocopherols) is also a known antioxidant. Vitamin E also provides sperm nutritional support and improves sperm quality, including concentration, motility and morphology. More significantly, the presence (e.g., regular administration) of vitamin E has shown to significantly improve pregnancy rate and live birth rate of men/couples undergoing artificial reproductive therapy, especially when used in conjunction with other antioxidants. The amount of vitamin E present in a single serving size of a composition of the invention is at least about 50 IU, typically at least about 100 IU, often at least about 150 IU and more often at least 200 IU.

Vitamin K (e.g., 50% as K1 and 50% as K2) is an essential nutrient for general overall health of human. For example, vitamin K has been shown to be important for heart health and bone health. Dietary deficiency of vitamin K is common. The amount of vitamin K present in a single serving size of a composition of the invention is at least about 40 mcg, typically at least about 50 mcg, often at least about 60 mcg and more often at least 80 mcg.

In some embodiments, compositions of the invention also include thiamin (e.g., as thiamine hydrochloric acid salt and/or benfotiamine). The amount of thiamine present in a single service size of compositions of the invention is about 1 mg, typically at least 2 mg and often at least 3 mg.

Compositions of the invention can also include riboflavin. When present, riboflavin is typically present as riboflavin 5 phosphate. The amount of riboflavin present in a single serving size of compositions of the invention is at least about 1 mg, typically at least about 2 mg and often at least about 3.4 mg.

Yet in other embodiments, compositions of the invention can also include niacin, e.g. as niacinamide. When present, the amount of niacin present in a single service size of compositions of the invention is at least about 5 mg, typically at least about 10 mg and often at least about 20 mg.

In some embodiments, compositions of the invention also include vitamin B6. Typically as pyridoxal 5 phosphate. When present, the amount of vitamin B6 in a single serving size comprises at least about 5 mg, typically at least about 10 mg, often at least about 20 mg and most often at least about 25 mg.

B Complex Vitamins are often referred to as a "B vitamins" or "vitamin B complex." Vitamin B complex has been shown to work to support energy production and cell division, which also supports sperm production and function. Typically, B vitamins are supplemented together.

B9/Folate (e.g., as QUATREFOLIC® (glucosamine salt of (6S)-5-methyltetrahydrofolate)) are also a known antioxidant. Administration of QUATREFOLIC® has shown to improve spermatogenesis and boost sperm quality. More significantly administration of QUATREFOLIC® has shown to significantly improve pregnancy rates, i.e., enhance male fertility. The amount of folate present in a single serving size of compositions of the invention is at least about 200 mcg, typically at least about 400 mcg, often at least about 600 mcg and most often at least about 800 mcg.

Vitamin $B_{12}$ (e.g., as methylcobalamin) is involved in cellular replication. Its deficiency leads to reduced sperm count and motility. Therefore, in some embodiments, compositions of the invention include vitamin $B_{12}$. Typically, the amount of vitamin $B_{12}$ in a single serving size of compositions of the invention is at least about 250 mcg, typically at least about 500 mcg, often at least 750 mcg and most often at least 1000 mcg.

Still in other embodiments, compositions of the invention can also include biotin (e.g., as d-biotin). When present, the amount of biotin in a single serving size of compositions of the invention is at least about 200 mcg, typically at least about 400 mcg and often at least about 600 mcg.

Another ingredient that can be included in compositions of the invention is pantothenic acid (e.g., as a calcium salt). When present, the amount of pantothenic acid present in a single serving size of compositions of the invention is at least about 5 mg, typically at least about 10 mg, often at least about 15 mg and most often at least about 20 mg.

Iodine (e.g., as potassium iodide) is necessary for the production of thyroid hormones which in turn affects male fertility. It should be noted with modern diet, iodine deficiency is becoming increasingly common. Thus, in some embodiments, compositions of the invention also include iodine. Typically the amount of iodine in a single serving size of compositions of the invention is at least about 50 mcg, typically at least about 100 mcg and often at least about 150 mcg.

Zinc (e.g., as zinc citrate) increases motility and concentration of sperm. It also enhances sperm maturation and testosterone synthesis. It is also believed that zinc acts as an antioxidant that counteracts reactive oxygen species. The presence of zinc improves sperm quality, and therefore, significantly improves pregnancy rate. It also increases live birth rate, along with vitamins and carnitines. In particular, improvement in live birth rate of men/couples undergoing artificial reproductive therapy is observed when used in conjunction with other antioxidants. When present, the amount of zinc in a single serving size of compositions of the invention is at least about 10 mg, typically at least about 20 mg and often at least about 30 mg.

Selenium is also a known antioxidant. It has been shown that selenium participates in sperm production and enhances sperm quality. Use of selenium has shown a significant improvement in pregnancy rate, as well as improvement in live birth rate of men/couples undergoing artificial reproductive therapy when used in conjunction with other antioxidants. Compositions of the invention can also include selenium, typically as 1-selenomethionine. When present, the amount of selenium in a single size serving of compositions of the invention is at least about 60 mg, typically at least about 100 mg and often at least about 140 mg.

Copper has been shown to participate in as an electron donor in biological reactions. Thus, it is believed it can counteract effects of reactive oxygen species. Compositions of the invention can also include copper, e.g., as copper sulfate. When present, the amount of copper in a single size serving of compositions of the invention is at least about 1 mg.

Manganese is an essential mineral for enzymes that protect the mitochondria from reactive oxygen species. Thus, the presence of manganese is believed to reduce the male infertility due to oxidative stress. Accordingly, in some embodiments, compositions of the invention also include manganese, typically as manganese bisglycinate chelate. When present, the amount of manganese in a single size serving of compositions of the invention is at least about 1 mg and often at least about 2 mg.

Chromium has been shown to help regulate sugar metabolism by working with insulin. Thus, it is believed that the presence of chromium is essential for overall health of human in general. Accordingly, in some embodiments, compositions of the invention include chromium as chromium polynicotinate. When present, the amount of chromium in a single size serving of compositions of the invention is at least about 60 mg, typically at least about 90 mg and often at least about 120 mg.

Molybdenum is essential for virtually all life forms. It has been shown molybdenum helps conversion of sulfur into useable form in the body. Accordingly, the presence of molybdenum improves overall general health of human. Thus, compositions of the invention can also include molybdenum. Typically molybdenum is present as molybdenum glycinate chelate. When present, the amount of molybdenum in a single size serving of compositions of the invention is at least about 25 mg, typically at least about 50 mg and often at least about 75 mg.

In addition to studies and functions discussed above, L-carnitine is vitamin-like compound that helps transport fatty acids into mitochondria where fatty acids are used as energy. L-carnitine helps sperm cells create energy needed for motility, and appears to prevent apoptosis. In some studies, L-carnitine has been shown to increase semen volume and motility. Moreover, L-carnitine has been shown to significantly improve pregnancy rate and also increase in live birth rate, especially when used in conjunction with vitamins and zinc. Typically, L-carnitine is present in compositions of the invention in a tartrate form. The amount of L-carnitine tartrate present in a single size serving of compositions of the invention is at least about 500 mg, typically at least about 1000 mg, often at least about 1500 mg and most often at least about 2000 mg.

Coenzyme Q10 is a known antioxidant that is believed to protect sperm cells. Studies have shown a correlation between higher concentration of coenzyme Q10 in seminal fluids with the higher sperm count. Among other benefits, coenzyme Q10 improves live birth rate of men/couples undergoing artificial reproductive therapy, especially when used in conjunction with other antioxidants. Typically, coenzyme Q10 is present as ubiquinone in compositions of the invention. The amount of coenzyme Q10 present in a single size serving of compositions of the invention is at least about 50 mg, typically at least about 100 mg, often at least about 150 mg and most often at least about 200 mg.

N-Acetyl L-cysteine improves live birth rate of men/couples particularly those undergoing artificial reproductive therapy. Typically, N-acetyl L-cysteine is used in conjunction with other antioxidants. The amount of N-acetyl L-cysteine present in a single size serving of compositions of the invention is at least about 50 mg, typically at least about 100 mg, often at least about 150 mg and most often at least about 200 mg.

Grape Seed Extract are well known powerful antioxidant. Various animal studies have shown grape seed extract comprising at least 80%, typically at least 85% polyphenols are effective in protecting against reproductive toxicity due to oxidative stress. It also has shown to have a rejuvenating effect. In some embodiments, compositions of the invention include grape seed extracts that have at least about 80%, typically at least about 85% polyphenols. The amount of grape seed extract present in a single size serving of compositions of the invention is at least about 5 mg, typically at least about 10 mg, often at least about 15 mg and most often at least about 20 mg.

Lycopene is another well known antioxidant. Lycopene enhances sperm quality, including count and viability and significantly improves pregnancy rate. It is believed lycopene increases the likelihood of successful pregnancy in spontaneous (i.e., "natural") and in vitro fertilization conception. Accordingly, some embodiments of compositions of the invention include lycopene. The amount of lycopene present in a single size serving of compositions of the invention is at least about 2 mg, typically at least about 5 mg, often at least about 8 mg and most often at least about 10 mg.

Benfotiamine is an effective metabolic precursor of active thiamine and helps ensure thiamine levels are sufficient. Benfotiamine is believed to prevent or reduce male infertility due to oxidative stress. When present, typically about 1 mg of benfotiamine is present in compositions of the invention.

L-Arginine (e.g., as hydrochloric acid salt form) is an amino acid that is necessary for sperm production. L-arginine is also a precursor for production of nitric oxide, which is required for sperm motility and erectile function. Thus, in some embodiments, compositions of the invention include L-arginine. When present, the amount of L-arginine present in a single size serving of compositions of the invention is at least about 100 mg, typically at least about 200 mg, often at least about 300 mg and most often at least about 350 mg.

In some embodiments, nutritional supplement compositions of the invention comprise N-acetyl L-cysteine. In other embodiments, nutritional supplement compositions of the invention comprise L-carnitine tartrate, coenzyme Q10, methylcobalamin, N-acetyl L-cysteine, and grape seed extract.

Typically a single unit of a composition (e.g., a single solid unit of capsule, tablet, caplet, gel, a single vial of liquid suspension, etc.) comprises at least about 5 mg, typically at least about 10 mg, more often at least about 20 mg, and most often at least about 30 mg of N-acetyl L-cysteine. It should be appreciated that the term "single unit" does not mean a "single serving size". In fact, in some embodiments, a single serving size may comprise two or three "single unit" formulation of the composition of the invention. For example, in some embodiments, the method of improving or enhancing male fertility comprises administering at least about 50 mg, typically at least about 100 mg, often at least about 150 mg and more often at least about 200 mg of N-acetyl L-cysteine per day. Thus, if a single unit of composition of the invention comprises 20 mg of N-acetyl L-cysteine, a single serving size will comprise ten of these single units to reach 200 mg of N-acetyl L-cysteine administration per day.

In some embodiments, the ratio of L-carnitine tartrate to coenzyme Q10 in a single unit is at least about 5:1, typically at least about 8:1 and often at least about 10:1. Yet in other embodiments, the ratio of L-carnitine tartrate to N-acetyl L-cysteine in a single unit is at least about 5:1, typically at least about 8:1 and often at least about 10:1. Still in another embodiments, the ratio of L-carnitine tartrate to vitamin $B_{12}$ in a single unit is at least about 1:1, typically at least about 1.5:1 and often at least about 2:1.

Typically, compounds of the invention are administered as nutritional supplement formulations suitable for oral administration. However, it should be appreciated that the scope of the invention is not limited to such a mode of administration. Typical manner of administration is generally oral using a convenient daily dosage regimen (e.g., "single serving amount") that can be adjusted according to the unit dosage (i.e., "single unit") formulation.

Compositions of the invention, together with one or more conventional adjuvants, carriers, or diluents, can be placed into the form of nutritional supplement compositions and unit dosages. The nutritional supplement compositions and unit dosage forms can be comprised of conventional ingredients in conventional proportions, with or without additional active components or principles, and the unit dosage ("single unit") forms can contain any suitable effective amount of the desired components commensurate with the intended daily dosage range to be employed. The nutritional supplement compositions can be employed as solids, such as tablets or filled capsules, semisolids, powders, sustained release formulations, or liquids such as solutions, suspensions, emulsions, elixirs, or filled capsules for oral use.

The compositions of the invention can be formulated in a wide variety of oral administration dosage forms. The nutritional supplement compositions and dosage forms can comprise a various components of the invention. The pharmaceutically acceptable carriers can be either solid or liquid. Solid form preparations include powders, tablets, pills, capsules, cachets and dispersible granules. A solid carrier can be one or more substances that can also act as diluents, flavoring agents, solubilizers, lubricants, suspending agents, binders, preservatives, tablet disintegrating agents, or an encapsulating material. In powders, the carrier generally is a finely divided solid that is mixed with the finely divided components of the invention. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the composition of the invention with encapsulating material as carrier, providing a capsule in which the composition of the invention, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the composition of the invention in water and adding suitable colorants, flavors, stabilizers, and thickening agents. Aqueous suspensions can be prepared by dispersing the finely divided composition of the invention in water with viscous material, such as natural or synthetic gums, resins, methylcellulose, sodium carboxymethylcellulose, and other well known suspending agents. Solid form preparations include solutions, suspensions, and emulsions, and can contain, in addition to the composition of the invention, colorants, flavors, stabilizers, buffers, artificial and natural sweeteners, dispersants, thickeners, solubilizing agents, and the like.

When desired, the composition of the invention can be formulated with enteric coatings adapted for sustained or controlled release administration of the composition of the invention.

The composition of the invention is typically in unit dosage forms. As discussed in detail herein, a single serving can include more than one unit dosage form of compositions of the invention. For example, a single service size can comprise two, three, four, five or six or more unit dosage forms. In such form, the preparation is often subdivided into unit doses containing appropriate quantities of the compositions of the invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1: Preparation of a Single Unit of a Composition of the Invention

Nutritional supplement capsules were produced using a conventionally known process. A single serving consisting of 6 capsules, i.e., each unit of capsule constituted ⅙ of daily recommended dosage of various components. Nutritional supplements were formulated such that 6 capsules (i.e., a single serving size) had the following quantities of compositions of the invention: β-carotene (5000 IU), ascorbic acid (120 mg), cholecalciferol (1200 IU), vitamin E (200 IU), vitamin K (80 mcg), thiamin (3 mg), riboflavin (3.4 mg), niacin (20 mg), vitamin B6 (25 mg), folate (800 mcg), vitamin $B_{12}$ (1000 mcg), biotin (600 mcg), pantothenic acid (20 mg), iodine (150 mcg), zinc (30 mg), selenium (140 mcg), copper (1 mg), manganese (2 mg), chromium (120 mcg), molybdenum (75 mcg), L-carnitine L-tartrate (2000 mg), L-arginine HCl (350 mg), coenzyme Q10 (200 mg), N-acetyl L-cysteine (200 mg), grape seed extract (20 mg), lycopene (10 mg) and benfotiamine (1 mg). Capsules also contained emulsifiers and binders such as vegetable capsule, microcrystalline cellulose, magnesium stearate and silicon dioxide.

Example 2: Efficacy

A control group of males and a test group of males, all of whom are having difficulty conceiving with their partner, are selected for testing. Each group is then further divided based on ethnicity and age range. Groups can be further subdivided based on a use of any similar medication, presence of any disease (e.g., diabetes), body mass index, similar alcohol consumption, and other factors. Control group is given placebo and the test group is given the nutritional supplement of Example 1. The rate of conception is followed each month for a year and is separated by in vitro fertilization or "natural" conception. The result is expected to show the test group receiving nutritional supplement of Example 1 will show higher rate of conception compared to the control group. It is expected the test group will show at least 5%, typically at least 10% and often at least 20% improvement in conception rate compared to the control group.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A nutritional supplement composition for improving male fertility comprising an effective amount of L-carnitine, coenzyme Q10, Vitamin $B_{12}$, N-acetyl L-cysteine, grape seed extract, biotin, molybdenum, and lycopene, wherein a single serving size of the composition contains at least about 25 mg of molybdenum.

2. The nutritional supplement composition of claim 1, wherein a single unit of said composition further comprises lycopene.

3. The nutritional supplement composition of claim 1, wherein a single unit of said composition further comprises an antioxidant, vitamins, minerals or a combination thereof.

4. The nutritional supplement composition of claim 1, wherein L-carnitine is L-carnitine tartrate, and wherein the ratio of L-carnitine tartrate to coenzyme Q10 in a single unit is at least about 5:1.

5. The nutritional supplement composition of claim 1, wherein the ratio of L-carnitine tartrate to N-acetyl L-cysteine in a single unit is at least about 5:1.

6. The nutritional supplement composition of claim 1, wherein L-carnitine is present as L-carnitine tartrate.

7. The nutritional supplement composition of claim 6, wherein the ratio of L-carnitine tartrate to vitamin $B_{12}$ in a single unit is at least about 1:1.

8. The nutritional supplement composition of claim 1, wherein a single unit of said composition comprises at least 25 mg of N-acetyl L-cysteine.

9. The nutritional supplement composition of claim 1, wherein a single serving of said composition comprises at least 100 mg of N-acetyl L-cysteine.

10. The nutritional supplement composition of claim 1 further comprising selenium, zinc, copper, manganese, chromium, or a combination thereof.

11. The nutritional supplement composition of claim 1 further comprising vitamin A, vitamin C, vitamin D3, vitamin E, vitamin K, thiamin, riboflavin, niacin, vitamin $B_6$, QUATREFOLIC® (glucosamine salt of (6S)-5-methyltetrahydrofolate), pantothenic acid, iodine, or a combination thereof.

12. The nutritional supplement composition of claim 1 further comprising L-arginine.

13. A method for improving fertility in a male human comprising administering to said male human an effective amount of a composition of claim 1.

14. The method of claim 13, wherein said composition is administered one to three unit dosage formulation per day to said male human.

15. The method of claim 13, wherein said composition is administered to said male human for at least 3 months.

* * * * *